US005268468A

United States Patent [19]

Effland et al.

[11] Patent Number: 5,268,468

[45] Date of Patent: Dec. 7, 1993

[54] N-NITROSOPHENOXYBENZENE-PROPANAMINE AND N-1-CHLOROETHYL CARBAMATE INTERMEDIATES

[75] Inventors: Richard C. Effland; Joseph T. Klein, both of Bridgewater, N.J.

[73] Assignee: Hoechst-Roussel Pharmaceuticals Incorporated, Somerville, N.J.

[21] Appl. No.: 65,298

[22] Filed: May 24, 1993

Related U.S. Application Data

[62] Division of Ser. No. 802,599, Dec. 5, 1991, Pat. No. 5,229,417.

[51] Int. Cl.$^5$ .................. C07C 207/04; C07C 271/16

[52] U.S. Cl. ....................................... 560/27; 564/112

[58] Field of Search .......................... 564/112; 560/27

[56] References Cited

U.S. PATENT DOCUMENTS

| | | | |
|---|---|---|---|
| 4,018,895 | 4/1977 | Molloy | 514/651 |
| 4,584,404 | 4/1986 | Molloy | 564/347 |
| 4,626,549 | 12/1986 | Molloy | 514/651 |

FOREIGN PATENT DOCUMENTS

| | | |
|---|---|---|
| 218005 | 4/1961 | Austria . |
| 1098950 | 2/1961 | Fed. Rep. of Germany . |
| 455825 | 7/1968 | Switzerland . |

*Primary Examiner*—Richard L. Raymond
*Attorney, Agent, or Firm*—Raymond R. Wittekind

[57] ABSTRACT

Novel 2-(3-phenylpropyl)hydrazines, intermediates in and processes for the preparation thereof, and a method of treating personality disorders utilizing compounds or compositions thereof are disclosed.

3 Claims, No Drawings

N-NITROSOPHENOXYBENZENEPROPANAMINE AND N-1-CHLOROETHYL CARBAMATE INTERMEDIATES

This is a division of application Ser. No. 07/802,599 filed Dec. 5, 1991, now U.S. Pat. No. 5,229,417.

The present invention relates to 2-[3-phenylpropyl]-hydrazines. More particularly, the present invention relates to 2-[3-phenyl-3-(phenoxy)propyl]hydrazines of formula 1

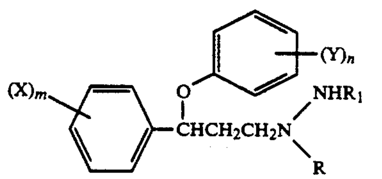

1 wherein R is hydrogen or loweralkyl; $R_1$ is hydrogen, loweralkyl, arylloweralkyl, a group of the formula

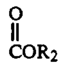

wherein $R_2$ is loweralkyl, or a group of the formula

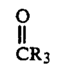

wherein $R_3$ is hydrogen, loweralkyl, aryl, or arylloweralkyl; X and Y are hydrogen, loweralkyl, loweralkoxy, halogen, or trifluoromethyl; m and n are independently 1 or 2; the optical isomers thereof; or the pharmaceutically acceptable acid addition salts thereof, which are useful for treating personality disorders such as obsessive compulsive disorders, alone or in combination with inert personality disorder treating adjuvants.

The present invention also relates to N-nitrosophenoxybenzenepropanamines of formula 2

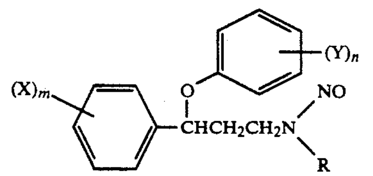

2 wherein R is loweralkyl and X, Y, m, and n are as hereinbefore described, which are useful as intermediates for the preparation of the instant 2-[3-phenyl-3-(phenoxy)propylhydrazines.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "aryl" refers to a phenyl group substituted by one or more alkyl, alkoxy, halogen, or trifluoromethyl groups; the term "halogen" refers to a member of the family consisting of chlorine, fluorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 2-[3-phenyl-3-(phenoxy)propyl]hydrazines of formula 1, compounds of the present invention, are prepared as shown in the Reaction Scheme by reducing a methylaminopropiophen-3-one 3, which is described by B. B. Molloy and K. K. Schmiegel in U.S. Pat. No. 4,018,895, issued Apr. 19, 1977, to a methylaminopropiophen-3-ol 4, which is condensed with a halobenzene 5

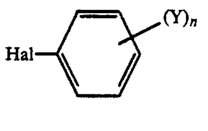

5 wherein Hal is fluoro or chloro, and Y and n are as hereinbeforedescribed, to a phenoxybenzenepropanamine 6 (wherein R is alkyl) and, in turn, demethylated to an N-alkylphenoxybenzenepropanamine 9 (wherein R is alkyl), nitrosated to an N-nitroso-3-phenoxybenzenepropanamine 2 and reduced to an N-amino-3-phenoxybenzenepropanamine 1. The reduction of propiophenone 3 to propanol 4 is conveniently performed by contacting 3 with an alkali metal borohydride such as, for example, lithium borohydride, potassium borohydride, or sodium borohydride, sodium borohydride being preferred, in an alkanol, or mixture thereof, such as, for example, methanol, ethanol, 1- or 2-propanol, butanol, 1- or 2-pentanol, 3-hexanol, or 4-heptanol, or mixtures of methanol or ethanol with each other, 2-propanol, or the other mentioned carbinols. A mixture of methanol and 2-propanol is the preferred solvent. The reduction proceeds at a reasonable rate at ambient temperature; higher reaction temperatures consistent with the solvent system may be employed, however. Ambient temperature is preferred.

The condensation is conducted by forming an anion of a propanol 4 with an alkali metal hydride, for example, lithium hydride, potassium hydride, or sodium hydride, or an oil-dispersion thereof, in a polar aprotic solvent, for example, dimethylacetamide, dimethylformamide, hexamethylphosphoramide, or dimethyl sulfoxide, and treating the anion so formed, preferably at ambient temperature, with a halobenzene 5, also preferably at ambient temperature. Sodium hydride-in-oil and dimethylformamide is the preferred medium for anion formation. A fluorobenzene, i.e., a halobenzene wherein Hal is fluoro, is the preferred condensation electrophile.

The dealkylation is effected by treating an N-alkyl-N-methylaminophenoxybenzenepropanamine 6 wherein R is alkyl with 1-chloroethyl chloroformate 7

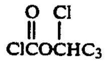 7 to provide an N-1-chloroethyl carbamate of formula 8

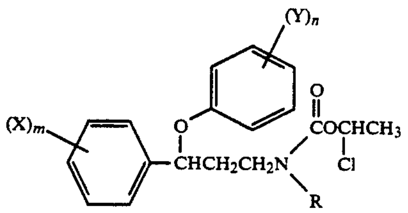 8 wherein R is alkyl and X, Y, m, and n are as hereinbeforedescribed, which is converted to an N-alkylaminophenoxybenzenepropanamine 9 wherein R is alkyl, and X, Y, m, and n are as hereinbeforedescribed. Demethylation with carbamate formation is carried out in a halocarbon, e.g., 1,1- or 1,2-dichloroethane, in the presence of an acid acceptor, e.g., a trialkylamine such as triethylamine at an elevated temperature within the range of about 70° to 115° C., a reaction temperature between 90° and 95° C. being preferred. 1,2-Dichloroethane and triethylamine are the preferred solvent and acid acceptor, respectively. The conversion of carbamate 8 to propanamine 9 is carried out under conventional conditions in a boiling alkanol. Among alkanols there may be mentioned methanol, ethanol, 1-, or 2-propanol, methanol being preferred.

The nitrosation is accomplished by subjecting an N-alkyl-3-phenoxybenzenepropanamine 9 wherein R is alkyl, and X, Y, m, and n are as hereinbeforedescribed to an alkali metal nitrite in an aqueous mineral acid at about ambient temperature. Included among alkali metal nitrites and aqueous mineral acids are, lithium nitrite, potassium nitrite, and sodium nitrite, and hydrochloric acid, hydrobromic acid, sulfuric acid, and nitric acid, respectively. Sodium nitrite and hydrochloric acid are preferred. Dilute hydrochloric acid, about 10% hydrochloric acid, is most preferred.

The reductive conversion of an N-nitroso-3-phenoxybenzenepropanamine 2 to a 2-[3-phenyl-3-(phenoxy)-propyl]hydrazine 1 is achieved by contacting an N-nitrosoamine 2 with zinc, preferably as dust, in acetic acid at ambient temperature.

An alkoxycarbonyl derivative 11 wherein $R_2$ is alkyl is prepared by treating a 2-[3-phenyl-3-(phenoxy)-propyl]hydrazine 1 with an alkyl haloformate 10

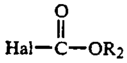 10 wherein Hal is chloro or bromo and $R_2$ is alkyl, for example, ethyl chloroformate, in a halocarbon, for example, dichloromethane, in the presence of an acid acceptor, for example triethylamine, at ambient temperature.

A 1-alkoxycarbonyl-2-[3-phenyl-3-(phenoxy)propyl]-hydrazine 11 may be reduced to a 1-methyl-2-[3-phenyl-3-(phenoxy)propyl]hydrazine 15 by methods well-known in the art such as those employing lithium aluminum hydride in ether.

An N-acyl derivative 14 wherein $R_3$ is as hereinbeforedescribed may be prepared by treating a 2-[3-phenyl-3-(phenoxy)propyl]hydrazine 1 with a carboxylic acid anhydride 12 or carboxylic acid chloride 13

 12

 13 under conditions well-known in the art.

An N-acyl-2-[3-(phenyl-3-(phenoxy)propyl]hydrazine 14 may be reduced to an 1-substituted-2-[3-phenyl-3-(phenoxy)propyl]hydrazine 15 wherein $R_1$ is loweralkyl or phenylloweralkyl by methods well-known in the art such as those employing lithium aluminum hydride in ether or borane in tetrahydrofuran.

The 2-[3-phenyl-3-(phenoxy)propyl]hydrazines of the present invention are useful for the treatment of personality disorders particularly obsessive compulsive disorders due to their ability to block serotonin uptake in mammals as determined in the assay described below:

$[^3H]$-Serotonin Uptake in Rat Whole Brain and Hypothalamic Synaptosomes

Procedure:

A. Animals: Male CR Wistar rats (100–125 g).

B. Reagents

1. Krebs-Henseleit Bicarbonate Buffer, pH 7.4 (KHBB): Make a 1 liter batch, containing the following salts.

| | grams/L | mM |
|---|---|---|
| Sodium chloride | 6.92 | 118.4 |
| Potassium chloride | 0.35 | 4.7 |
| Magnesium sulfate heptahydrate | 0.29 | 1.2 |
| Potassium dihydrogen phosphate | 0.16 | 2.2 |
| Sodium bicarbonate | 2.10 | 24.9 |
| Calcium chloride | 0.14 | 1.3 |
| Prior to use add: | | |
| Dextrose | 2 mg/ml | 11.1 |
| Iproniazid phosphate | 0.30 mg/ml | 0.1 |

Aerate for 60 min. with 95% oxygen/5% carbon dioxide, check pH (7.4 ± 0.1)

2. 0.32 M Sucrose: 21.9 g of sucrose, bring to 200 ml.
3. Serotonin creatinine sulfate 0.1 mM stock solution is made up in 0.01 N hydrochloric acid. This is used to dilute the specific activity of radiolabeled $[H^3]$-5-hydroxytryptamine (serotonin).
4. 5-$[1,2\text{-}^3H(N)]$-Hydroxytryptamine creatinine sulfate (Serotonin), specific activity 20–30 Ci/mmol is used. The final desired concentration of $[H^3]$-5-hydroxytryptamine in the assay is 50 nM. The dilution factor is 0.8. Therefore, the KHBB is made up to contain 62.5 nM $[H^3]$-5-hydroxy-tryptamine.
   Add to 100 ml of KHBB:
   A) 56.1 μl of 0.1 mM 5-hydroxytryptamine = 56.1 nM
   *B) 0.64 nmole of 5-hydroxytryptamine = 6.4 nM
   62.5 nM
5. For most assays, a 1 mM stock solution of the test compound is made up in suitable solvent and serially diluted such that the final concentration in the assay ranges from $2 \times 10^{-8}$ to $2 \times 10^{-5}$ M. Seven concentrations are used for each assay. Higher or lower concentrations may be used depending on the potency of the compound.

C. Tissue Preparation

Male Wistar rats are decapitated and the brain rapidly removed. Either whole brain minus cerebella or the hypothalamus is weighed and homogenized in 9 volumes of ice-cold 0.32 M sucrose using a Potter-Elvejhem -continued

| [$^3$H]-Serotonin Uptake in Rat Whole Brain and Hypothalamic Synaptosomes |
|---|
| homogenizer. Homogenization should be done with 4–5 up and down strokes at medium speeds to minimize synaptosome lysis. The homogenate is centrifuged at 1000 g for 10 min at 0–4° C. the supernatant ($S_1$) is decanted and is used for uptake experiments. |
| D. Assay |
| 800 μl KHBB + [$^3$H]-5-hydroxytryptamine |
| 20 μl Vehicle or appropriate drug concentration |
| 200 μl Tissue suspension |
| Tubes are incubated at 37° C. under a 95% oxygen/5% carbon dioxide atmosphere for 5 minutes. For each assay, 3 tubes are immediately centrifuged at 4000 g for 10 minutes. The supernatant fluid is aspirated and the pellets dissolved by adding 1 ml of solubilizer (Triton X-100 + 50% ethanol, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis. |

*Calculate volume added from specific activity of [$H^3$]-5-hydroxytryptamine

Presented in the Table are the inhibition of serotonin uptake for a compound of the present invention and a standard, expressed as the concentration at which 50% inhibition occurs, i.e., $IC_{50}$-values.

TABLE

| Compound | Inhibition of Serotonin Uptake ($IC_{50}$) |
|---|---|
| 2-methyl-2-[3-phenyl-3-[(4-trifluoromethyl)-phenoxy]propyl]hydrazine | 1.23 |
| N-methyl-3-(4-(trifluoromethyl)-phenoxy]benzenepropanamine (reference) | 0.25 |

Inhibition of serotonin uptake activity is achieved when the present 2-[3-phenyl-3-(phenoxy)propyl]hydrazines are administered to a subject requiring such treatment as an effective oral, parenteral or intravenous dose of from 0.01 to 50 mg/kg of body weight per day. A particularly effective amount is about 5 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such compositions is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Compounds of the invention include:

1. 2-[3-Phenyl-3-[(4-trifluoromethyl)phenoxy]propyl]-hydrazine;
2. 1,2-Dimethyl-2-[3-phenyl-3-[(4-trifluoromethyl)-phenoxy]propyl]hydrazine;

3. 2-[3-Phenyl-3-phenoxy]propylhydrazine;
4. 2-[3-Phenyl-3-[(2-methyl)phenoxy]propyl]hydrazine;
5. 2-[3-Phenyl-3-[(2-methoxy)phenoxy]propyl]hydrazine;
6. 2-[3-Phenyl-3-[(3-chloro)phenoxy]propyl]hydrazine;
7. 2-Methyl-2-[3-(2-methyl)phenyl-3-[(4-trifluoromethyl)phenoxy]propyl]hydrazine;
8. 2-Methyl-2-[3-(3-methoxy)phenyl-3-[(4-trifluoromethyl)phenoxy]propyl]hydrazine
9. 2-Methyl-2-[3-(4-bromo)phenyl-3-[(4-trifluoromethyl)phenoxy]propyl]hydrazine;
10. 2-Methyl-2-[3-(4-trifluoromethyl)phenyl-3-[(4-trifluoromethyl)phenoxy]propyl]hydrazine;
11. 1-Phenylmethyl-2-[3-phenyl-3-[(4-trifluoromethyl)-phenoxy]propyl]hydrazine;
12. Acetic acid 2-[3-phenyl-3-[(4-trifluoromethyl)-phenoxy]propyl]hydrazide;
13. Formic acid 2-[3-phenyl-3-[(4-trifluoromethyl)-phenoxy]propyl]hydrazide;
14. Benzoic acid 2-[3-phenyl-3-[(4-trifluoromethyl)-phenoxy]propyl]hydrazide; and
15. Phenylacetic acid 2-[3-phenyl-3-[(4-trifluoromethyl)phenoxy]propyl]hydrazide.

The following Examples are for illustrative purposes only and are not to be construed as limiting the invention.

EXAMPLE 1

N-Methyl-3-[4-(trifluoromethyl)phenoxy]benzenepropanamine hydrochloride

3-Dimethylaminopropiophenone hydrochloride (20 g) was treated with aqueous sodium bicarbonate solution in dichloromethane. The layers were separated and the organic phase was dried over anhydrous magnesium sulfate, filtered, and the filtrate was evaporated to provide 15.8 g of 3-dimethylaminopropiophenone.

Sodium borohydride (6.7 g) was slowly added to a solution of 3-dimethylaminopropiophenone (15.5 g) in 2-propanol (125 ml) and methanol (25 ml). After two hrs, the reaction mixture was stirred with water and extracted with ethyl acetate-ether. The organic extract was washed with water and saturated sodium chloride solution, dried over anhydrous magnesium sulfate, filtered, and the filtrate was evaporated to give 15.2 g (97%) of 3-dimethylamino-1-phenyl-1-propanol, as an oil. A solution of 3-dimethylamino-1-phenyl-1-propanol (15 g) in dimethylformamide (75 ml) was slowly added to a suspension of sodium hydride (60% oil-dispersion, washed with hexane, 5.5 g) in dimethylformamide (20 ml). A solution of 4-fluorobenzotrifluoride (18 g) in dimethylformamide (20 ml) was added. After two hrs, the reaction mixture was stirred with ice-water and extracted with ether. The ether extract was dried over anhydrous magnesium sulfate, filtered, and the filtrate was evaporated to provide 27 g (100%) of N,N-dimethyl-3-[4-(trifluoromethyl)phenoxy]benzenepropanamine.

1-Chloroethyl chloroformate (10 g) was added to a solution of N,N-dimethyl-3-[(4-trifluoromethyl)phenoxy]benzenepropanamine (15 g) in dichloroethane (150 ml) and triethylamine (7.5 g). The solution stirred for four hrs at 90°-95° C., cooled, stirred with water, and extracted with ether. The organic extract was washed with water and saturated sodium chloride, dried over anhydrous magnesium sulfate, filtered, and the filtrate was evaporated. The residue was flash chromatographed on silica (eluted with 20% ethyl acetate-dichloromethane) to yield 11.2 g (58%) of N-methyl-3-[4-(trifluoromethyl)phenoxy]benzenepropanamine N-1-chloroethyl carbamate, as an oil.

A solution of N-methyl-3-[4-(trifluoromethyl)-phenoxy]benzenepropanamine N-1-chloroethyl carbamate in methanol (100 ml) was stirred under reflux for one hr, cooled, stirred with water, basified with sodium carbonate solution, and extracted with ether. The organic extract was dried over anhydrous magnesium sulfate, filtered, and the filtrate was evaporated. The residue (8 g) was combined with 2 g of product obtained under similar conditions and flash chromatographed on silica (eluted with 10% methanol in dichloromethane) to yield 6.5 g (34%) of product, which was converted to the hydrochloride salt in ether. Recrystallization from 5% methanol in ether yielded the product as the hydrochloride, mp 154°-155° C.

ANALYSIS: Calculated for $C_{17}H_{19}ClF_3NO$: 59.05% C; 5.54% H; 4.05% N. Found: 59.12% C; 5.44% H; 4.04% N.

EXAMPLE 2

N-Methyl-N-nitroso-3-[4-(trifluoromethyl)phenoxy]-benzenepropanamine

A solution of sodium nitrite (7.2 g) in water (50 ml) was added slowly to a solution of N-methyl-3-[4-(trifluoromethyl)phenoxy]benzenepropanamine (30 g) and dichloromethane (100 ml) in 10% hydrochloric acid (200 ml). After one hr, the reaction mixture was separated, and the aqueous phase was extracted with dichloromethane. The organic extracts were dried over anhydrous magnesium sulfate, filtered, and the filtrate was evaporated. The residue was chromatographed on silica (eluted with 50% hexanes-dichloromethane). The appropriate fractions were collected and evaporated to give 28 g (95.4%) of product, mp 75°-76° C. Recrystallization from hexanes gave the analytical sample, mp 76°-77° C.

ANALYSIS: Calculated for $C_{17}H_{17}F_3N_2O_2$: 60.35% C; 5.06% H; 8.28% N. Found: 60.44% C; 4.92% H; 8.13% N.

EXAMPLE 3

2-Methyl-2-[3-phenyl-3-[(4-trifluoromethyl)phenoxy]-propyl]hydrazine maleate Zinc dust (12.6 g) was added to a solution of the N-methyl-N-nitroso-3-(4-trifluoromethyl)phenoxy]benzenepropanamine (13 g) in glacial acetic acid (120 ml) and water (60 ml). The reaction mixture was stirred at ambient temperature for four hrs. The mixture was filtered, stirred with ice, basified with ammonium hydroxide solution, and extracted with dichloromethane. The organic layer was washed with water and saturated sodium chloride solution, dried over anhydrous magnesium sulfate, filtered, and the filtrate was evaporated. The residue was eluted through silica with ethyl acetate via high performance liquid chromatography to yield 9.4 g (75.4%) of product. A four-gram portion was distilled twice utilizing a Kugelrohr apparatus (oven temperature 135°-140° C. @ 0.1 mm of mercury) to yield 3.8 g (72%) of distilled product. A three-gram portion was converted to the maleate salt in 10% methanol in ether to yield 3 g (53%) of product, mp 95°-97° C. Recrystallization from methanol in ether gave the analytical sample, mp 100°-101° C.

ANALYSIS: Calculated for $C_{21}H_{23}F_3N_2O_5$: 57.27% C; 5.26% H; 6.36% N. Found: 57.18% C; 5.24% H; 6.33% N.

EXAMPLE 4

2-Methyl-2-[3-phenyl-3-[(4-trifluoromethyl)phenoxy]-propyl]hydrazinecarboxylic acid ethyl ester A solution of ethyl chloroformate (3.7 g) in dichloromethane (20 ml) was added to an ice-cooled solution of 1-methyl-1-[3-phenyl-[(4-trifluoromethyl)phenoxy]-propyl]hydrazine (10 g) and triethylamine (7.3 g) in dichloromethane (100 ml). After one hr, the mixture was washed with water and saturated sodium chloride solution, dried over anhydrous magnesium sulfate, filtered, and the filtrate was evaporated. The residue was flashed chromatographed on silica, eluting with 5% ethyl acetate in dichloromethane. The appropriate fractions were collected and evaporated. Kugelrohr distillation of 3.1 g at 155°-150° C./0.01 mm of mercury afforded 2.8 g (70.2%) of product, mp 74°-76° C.

ANALYSIS: Calculated for $C_{20}H_{23}F_3N_2O_3$: 60.59% C; 5.85% H; 7.07% N. Found: 60.61% C; 5.71% H; 6.73% N.

We claim:

1. A compound of the formula

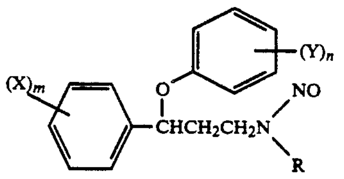

wherein R is loweralkyl; X and Y are hydrogen, loweralkyl, loweralkoxy, halogen, or trifluoromethyl; and m and n are independently 1 or 2, or the optical isomers thereof.

2. A compound according to claim 1 which is N-methyl-N-nitroso-3-[4-(trifluoromethyl)phenoxy]-propanamine.

3. N-Methyl-3-[4-(trifluoromethyl)phenoxy]benzene-propanamine-N-1-chloroethyl carbamate.

* * * * *

REACTION SCHEME

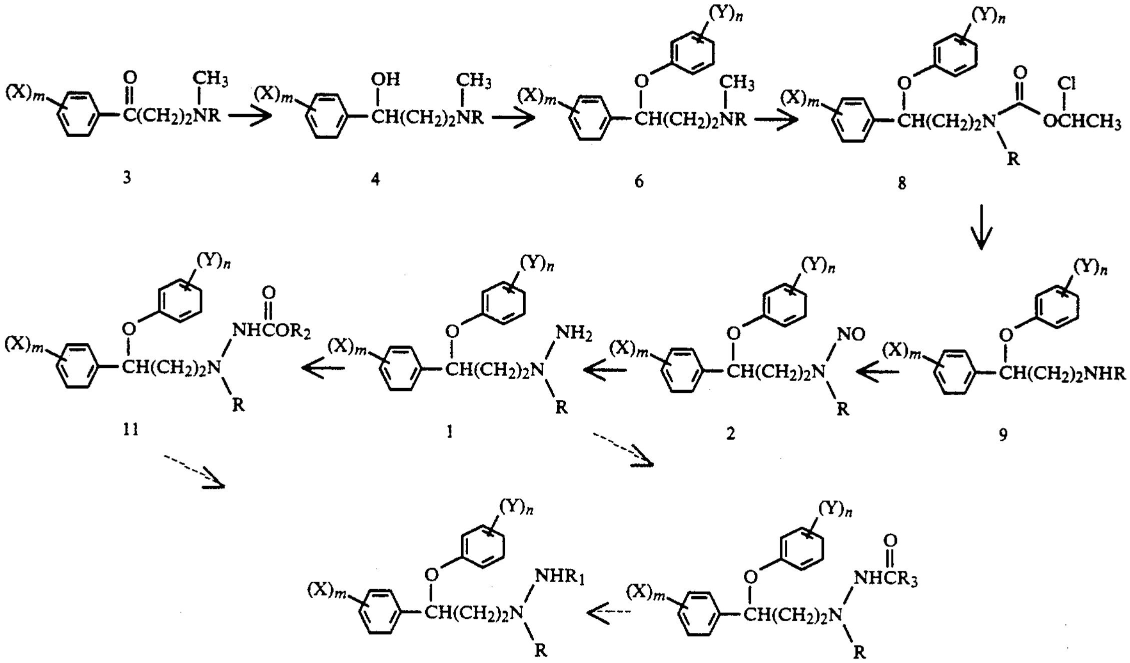

3 4 6 8

11 1 2 9

15 14

Where R, $R_1$, $R_2$, $R_3$, X, Y, m, and n are as hereinbeforedescribed